US00PP35533P2

(12) United States Plant Patent
Nahoum

(10) Patent No.: US PP35,533 P2
(45) Date of Patent: Dec. 12, 2023

(54) ***ANANAS* PLANT NAMED 'MILA'**

(50) Latin Name: ***Ananas* hybrid**
Varietal Denomination: Mila

(71) Applicant: Pedro Nahoum, Rio de Janeiro (BR)

(72) Inventor: Pedro Nahoum, Rio de Janeiro (BR)

( * ) Notice: Subject to any disclaimer, the term of this patent is extended or adjusted under 35 U.S.C. 154(b) by 0 days.

(21) Appl. No.: 18/111,020

(22) Filed: Feb. 17, 2023

(51) Int. Cl.
*A01H 5/08* (2018.01)
*A01H 6/22* (2018.01)

(52) U.S. Cl.
USPC ..... Plt./156
CPC ..... *A01H 6/22* (2018.05)

(58) Field of Classification Search
USPC ..... Plt./156
CPC ..... A01H 6/22; A01H 5/08
See application file for complete search history.

*Primary Examiner* — Keith O. Robinson
(74) *Attorney, Agent, or Firm* — Penny J. Aguirre

(57) ABSTRACT

A new cultivar of *Ananas* plant named 'Mila' that is characterized by its usefulness as an ornamental pineapple, its foliage that is red-orange in color when mature with the color retained very well (does not fade easily), its red fruit (infruitescence), and its highly vigorous growth habit with foliage fully developed between 5 to 7 months and fruit fully developed between 9 to 11 months.

3 Drawing Sheets

Botanical classification: *Ananas* hybrid.
Cultivar designation: 'Mila'.

CROSS REFERENCE TO A RELATED APPLICATIONS

This application is related to a plant breeders' rights application in Japan on Mar. 20, 2022, application No. 36191.

BACKGROUND OF THE INVENTION

The present invention relates to a new and distinct cultivar of *Ananas* of hybrid origin, botanically known as *Ananas* 'Mila' and is hereinafter referred to by the cultivar name 'Mila'. The new cultivar of ornamental pineapple plant grown for use in landscapes and containers.

The new cultivar arose from a cross made by the Inventor in Maricá, Rio de Janeiro, Brazil in 2008 between *Ananas comosus* 'Morada' (not patented) as the female parent and *Ananas erectifolius* 'Ceará' (not patented) as the male parent. The Inventor selected 'Mila' as a single unique plant amongst the seedlings that resulted from the above cross in 2010.

Asexual reproduction of the new cultivar was first accomplished by offsets (pups) by the Inventor in Maricá, Rio de Janeiro, Brazil in 2010. Asexual reproduction of the new cultivar by offsets and tissue culture using meristematic tissue has shown that the unique features are stable and reproduced true to type in successive generations

SUMMARY OF THE INVENTION

The following traits have been repeatedly observed and represent the characteristics of the new cultivar. These attributes in combination distinguish 'Mila' as a new and unique cultivar of *Ananas*.

1. 'Mila' exhibits usefulness as an ornamental pineapple.
2. 'Mila' exhibits foliage that is red-orange in color when mature with the color retained very well (does not fade easily).

3. 'Mila' exhibits red fruit (infruitescence).
4. 'Mila' exhibits a highly vigorous growth habit with foliage fully developed between 5 to 7 months and fruit fully developed between 9 to 11 months.

The female parent of 'Mila' differs from 'Mila' in having leaves that are purple in color with more leaf trichomes and with spines and larger fruit that is bright purple in color with juicier flesh. The male parent of 'Mila' differs from 'Mila' in having leaves that are narrower and shorter in size, held more upright in aspect, and lighter red in color with less leaf trichomes and fruit that is lighter red in color and much smaller in size. 'Mila' can be most closely compared to the *Ananas* cultivars 'Rosita' (not patented) and 'Amigo' (not patented). Both 'Rosita' and 'Amigo' are similar in having spineless leaves. Both 'Rosita' and 'Amigo' differ in having foliage that is all green in color.

BRIEF DESCRIPTION OF THE DRAWINGS

The accompanying color photographs illustrate the overall appearance and distinct characteristics of the new *Ananas*. The photographs were taken of a 6-month-old plant of 'Mila' as grown in a greenhouse in a 11-cm container in St. Oedenrode The Netherlands.

The photograph in FIG. 1 provides a view of the plant habit of 'Mila'.

Figure 1:
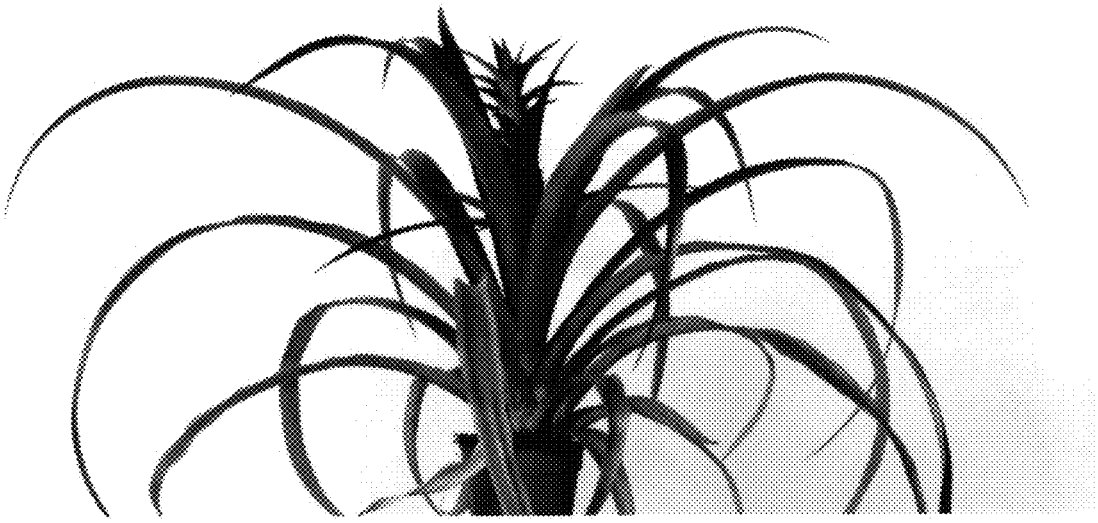
Figure 2:
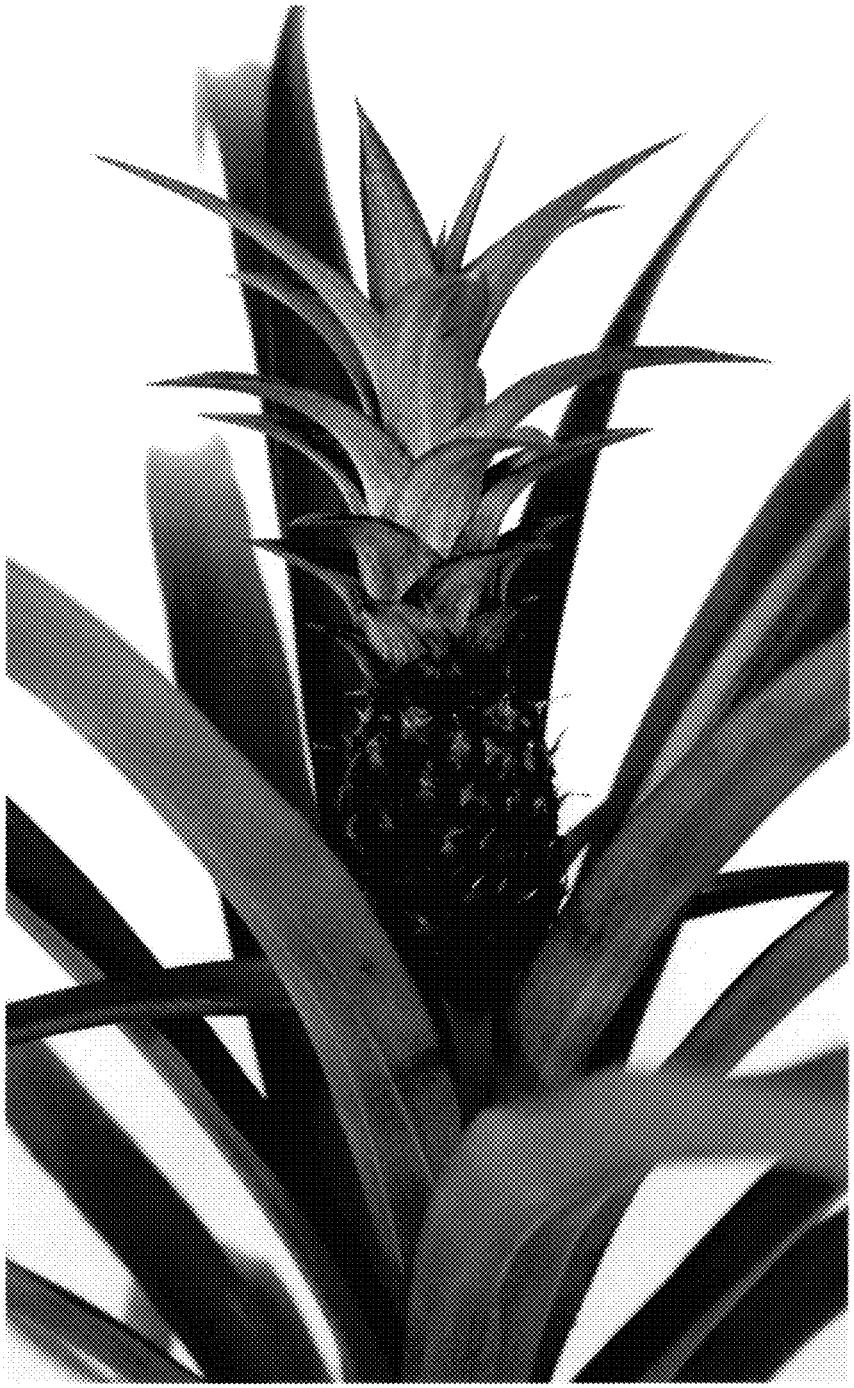

The photograph in FIG. 2 provides a close-up view of the fruit of 'Mila'.

Figure 3:
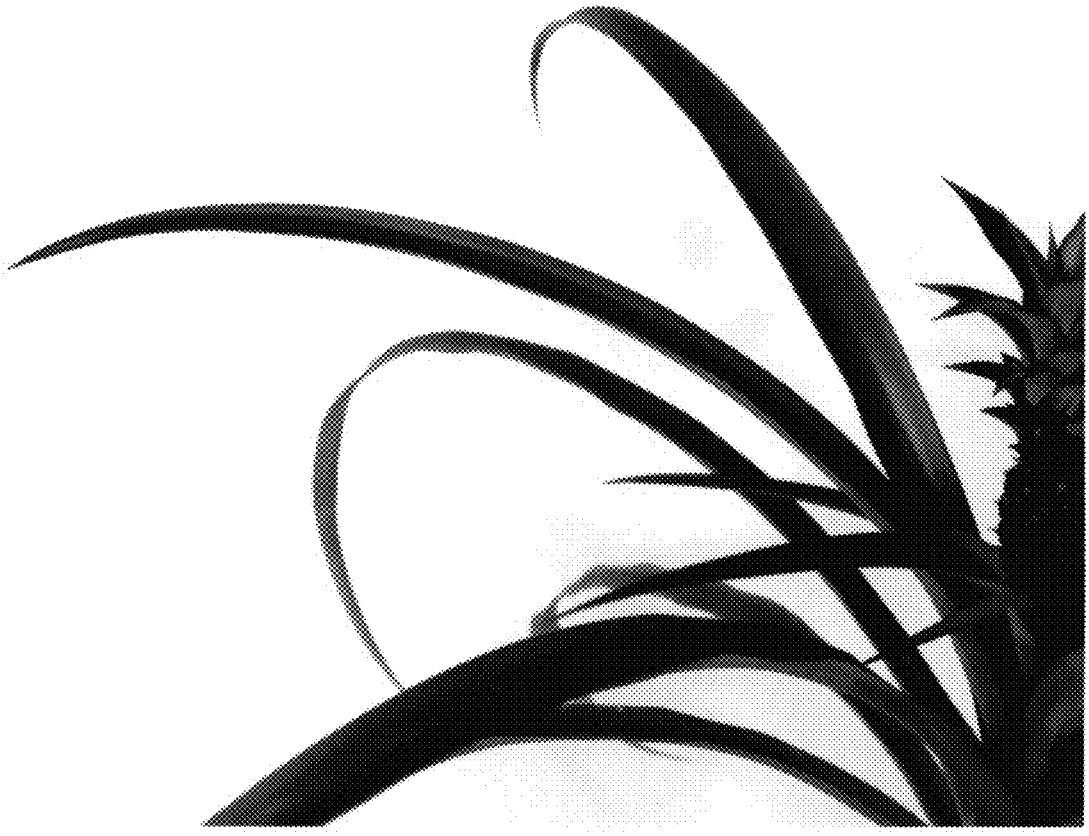

The photograph in FIG. 3 provides a close-up view of the foliage of 'Mila'.

The colors in the photographs are as close as possible with the photographic and printing technology utilized and the color values cited in the detailed botanical description accurately describe the colors of the new *Ananas*.

DETAILED BOTANICAL DESCRIPTION OF THE PLANT

The following is a detailed description of six-month-old plants of the new cultivar as grown in 11-cm containers in a greenhouse in St. Oedenrode The Netherlands. The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant habit*.—Herbaceous perennial, basal rosette with upright infructescence growing as a spike from the center.

*Plant shape*.—Upright with cascading foliage.

*Height and spread*.—About 45.5 cm in height and 94 cm in width.

*Cold hardiness*.—At least to U.S.D.A Zone 10.

*Diseases and pests*.—No susceptibility or resistance to pests has been observed.

*Root description*.—Rhizomes with fine, fibrous roots.

*Propagation*.—Tissue culture and offset (pup) division.

*Root development*.—From a tissue culture plantlet; foliage is fully developed between 5 to 7 months and fruit fully developed between 9 to 11 months.

*Growth rate*.—Highly vigorous.

Foliage description:

*Leaf quantity*.—Average of 28 per rosette.

*Leaf size*.—Average of 75.6 (excluding sheath), 3.3 cm in width.

*Leaf shape*.—Ligulate.

*Leaf division*.—Simple.

*Leaf base*.—Sheathing.

*Leaf apex*.—Long acuminate.

*Leaf venation*.—Parallel, upper surface color; 183A, margins tinged with 152A, outer edge of margin 146B, lower surface color; 182B, margins tinged with 146C.

*Leaf margins*.—Entire.

*Leaf aspect*.—Strongly arching, held in an average angle of 50° to soil level, tip pointed in an average angle of near to over vertical −90° to soil level.

*Leaf arrangement*.—Basal rosette.

*Leaf surface*.—Both sides glabrous, upper surface moderately glossy, lower surface matte.

*Leaf color*.—Young leaves upper surface; a blend of 183A and 187A and slightly darker, margins NN137B, young leaves lower surface; 182B, margins and apex 146B, leaf covered with a thin layer of 198C, mature leaves upper surface; 183A and slightly darker, margins 152A, outer edges of margins 146B, mature lower surface; 182B, margins and apex 146C, leaf covered with a thin layer of 198C.

*Leaf durability of foliage stresses*.—Very high.

*Sheath*.—Average of 8.7 cm in length, 6.1 cm in diameter, upper surface color a blend of 152D and 195A, changing to 182B at the leaf blade, lower surface color 148B, covered with a very thin layer of 194B.

Flower and fruit description:

*Blooming period*.—Flowers develop internally in fruit as an infructescence; 9 to 11 months from propagation.

*Inflorescence type*.—Spike, flowers borne internally on a hollow inverted receptacle, the flower itself is not visible as it blooms inside the infructescence.

*Peduncles*.—Average of 22 cm in length, 1.2 cm in diameter, straight upright, very strong, color; 200C, covered with a layer that is a blend of 197C and 198A.

*Scapes*.—Base scapes; at the base of the fruit are an average of 10 bract scapes, average of 12.8 cm in length, and 1.3 cm in width, apex is long acuminate, entire margins, sheathing base, color; upper surface 183A, margins a blend of 146B and 152B, proximal end N45C, lower surface 178B, apex 146C, proximal end a blend of 46A and 180A, covered with a thin layer of 198C, top scapes; on the crown (top) of the fruit are an average of 25 bract scapes, broadly lanceolate in shape, average of 4 cm in length, 2 cm in width, color; upper surface a blend of N186C and 200A, lower surface a blend of N187C and 200B, both surfaces covered with a layer of 146D.

*Seed*.—No seeds present.

*Fruit*.—1 infruitescence comprised of an average of 65 fruits, average of 5 mm in length, 1.2 cm in diameter, surface is glabrous and glossy, typical shape for *Ananas* (conical), ripens in an average of 4 weeks, color; 200A, tinged with a blend of N186C, 187A and 187B, tasteless, fruit is not suitable for consumption.

It is claimed:

1. A new and distinct cultivar of *Ananas* plant named 'Mila' as herein illustrated and described.

* * * * *